United States Patent
Brown et al.

(10) Patent No.: US 10,639,155 B2
(45) Date of Patent: May 5, 2020

(54) INFLATABLE PENILE PROSTHESIS WITH REVERSIBLE FLOW PUMP

(71) Applicant: Boston Scientific Scimed, Inc., Maple Grove, MN (US)

(72) Inventors: Nathan K. Brown, Bloomington, MN (US); Matthew Lee Nelson, Eden Prairie, MN (US); Patricia M. Derus, Rogers, MN (US); Douglas Lawrence Evans, Andover, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 217 days.

(21) Appl. No.: 15/689,551

(22) Filed: Aug. 29, 2017

(65) Prior Publication Data
US 2018/0064536 A1 Mar. 8, 2018

Related U.S. Application Data

(60) Provisional application No. 62/383,051, filed on Sep. 2, 2016.

(51) Int. Cl.
| | |
|---|---|
| *A61F 2/26* | (2006.01) |
| *F16K 11/065* | (2006.01) |
| *F04B 43/00* | (2006.01) |
| *F04B 33/00* | (2006.01) |
| *F04B 9/14* | (2006.01) |
| *F04B 53/10* | (2006.01) |

(52) U.S. Cl.
CPC .............. *A61F 2/26* (2013.01); *F04B 9/14* (2013.01); *F04B 33/00* (2013.01); *F04B 43/0063* (2013.01); *F04B 53/10* (2013.01); *F16K 11/0655* (2013.01); *A61F 2250/0003* (2013.01); *A61F 2250/0013* (2013.01)

(58) Field of Classification Search
CPC .............. A61F 2/26; A61F 2/00–0059; A61F 2250/0003; A61F 2250/0013
See application file for complete search history.

(56) References Cited

U.S. PATENT DOCUMENTS 3,744,063 A * 7/1973 McWhorter ............ A61F 2/004
623/23.66
3,863,622 A 2/1975 Buuck
(Continued)

OTHER PUBLICATIONS

International Search Report and Written Opinion for PCT Patent Application No. PCT/US2017/049306, dated Dec. 12, 2017, 16 pages.

*Primary Examiner* — Thaddeus B Cox
(74) *Attorney, Agent, or Firm* — Brake Hughes Bellermann LLP

(57) ABSTRACT

According to an aspect, an inflatable penile prosthesis includes an inflatable member, a reservoir configured to hold fluid, and a pump assembly configured to facilitate a transfer of the fluid from the reservoir to the inflatable member when the prosthesis is in an inflation mode and facilitate a transfer of the fluid from the inflatable member to the reservoir when the prosthesis is in a deflation mode. The pump assembly includes a pump, a valve body having a first valve and a second valve, and a selection member defining a lumen, the selection member being movable from a first position to place the prosthesis in the inflation mode and a second position to place the prosthesis in the deflation mode.

11 Claims, 14 Drawing Sheets

(56) References Cited

U.S. PATENT DOCUMENTS

| | | | |
|---|---|---|---|
| 4,958,630 A | 9/1990 | Rosenbluth et al. | |
| 8,939,889 B1* | 1/2015 | Chechik | A61F 2/26 600/40 |
| 2004/0147886 A1* | 7/2004 | Bonni | A61F 2/004 604/327 |
| 2007/0142700 A1 | 6/2007 | Fogarty et al. | |
| 2012/0157764 A1* | 6/2012 | Borgaonkar | A61F 2/26 600/40 |
| 2013/0072751 A1 | 3/2013 | Fogarty | |
| 2013/0263649 A1 | 10/2013 | Storch et al. | |
| 2014/0309490 A1* | 10/2014 | Lund | A61F 2/26 600/40 |
| 2015/0359655 A1* | 12/2015 | Daniel | A61F 5/41 600/40 |
| 2016/0008162 A1* | 1/2016 | Daniel | A61F 5/41 600/40 |
| 2016/0067044 A1* | 3/2016 | Daniel | A61F 2/26 600/40 |
| 2016/0081801 A1* | 3/2016 | Little | A61F 2/26 600/40 |
| 2016/0089241 A1* | 3/2016 | Taylor | A61F 2/26 600/40 |
| 2016/0100945 A1* | 4/2016 | Little | A61F 2/26 600/40 |
| 2016/0158014 A1* | 6/2016 | Daniel | A61F 2/26 600/40 |

\* cited by examiner

INFLATABLE PENILE PROSTHESIS WITH REVERSIBLE FLOW PUMP

CROSS-REFERENCE TO RELATED APPLICATION

This application is a Nonprovisional of, and claims priority to, U.S. Patent Application No. 62/383,051, filed on Sep. 2, 2016, entitled "INFLATABLE PENILE PROSTHESIS WITH REVERSIBLE FLOW PUMP", which is incorporated by reference herein in its entirety.

TECHNICAL FIELD

This disclosure relates to an inflatable penile prosthesis with a reversible flow pump and methods for operating the same.

BACKGROUND

One treatment for male erectile dysfunction is the implantation of a penile prosthesis that mechanically erects the penis. According to some existing designs of inflatable penile prostheses, the amount of time, energy and disparity from the occurrence of a normal human male erection for the patient to inflate a penile prosthesis (e.g., the number of pumps and time required to provide the desired penis rigidity) may be relatively high, and additionally transitioning to the deflation state may be relatively cumbersome.

SUMMARY

According to an embodiment, an inflatable penile prosthesis includes an inflatable member, a reservoir configured to hold fluid, and a pump assembly configured to facilitate a transfer of the fluid from the reservoir to the inflatable member when the prosthesis is in an inflation mode and facilitate a transfer of the fluid from the inflatable member to the reservoir when the prosthesis is in a deflation mode. The pump assembly includes a pump, a valve body having a first valve and a second valve, and a selection member defining a lumen, the selection member being movable from a first position to place the prosthesis in the inflation mode and a second position to place the prosthesis in the deflation mode.

In some embodiments, the lumen of the selection member is configured to be aligned with the first valve when the selection member is in the first position and is configured to be aligned with the second valve when the selection member is in the second position. In some embodiments, the selection member is movably coupled to the valve body. In some embodiments, the selection member is slidably coupled to the valve body.

In some embodiments, the first valve is a one-way valve. In some embodiments, the first valve is a one-way duckbill valve.

In some embodiments, the valve body includes a third valve and a fourth valve. In some embodiments, the valve body includes a third and a fourth valve, the lumen of the selection member is configured to be aligned with the first valve and the third valve when the selection member is in the first position and is configured to be aligned with the second valve and the fourth valve when the selection member is in the second position. In some embodiments, the valve body includes a third valve, a fourth valve, a fifth valve, and a sixth valve, the lumen of the selection member is configured to be aligned with the first valve, the third valve, and the fifth valve when the selection member is in the first position and is configured to be aligned with the second valve, the fourth valve, and the sixth valve when the selection member is in the second position.

In some embodiments, the valve body defines a first channel that fluidically couples the inflatable member and the pump, the valve body defines a second channel that fluidically couples the inflatable member and the pump, the first valve being disposed within the first channel, the second valve being disposed within the second channel. In some embodiments, the valve body defines a first channel that fluidically couples the reservoir and the pump, the valve body defines a second channel that fluidically couples the reservoir and the pump, the first valve being disposed within the first channel, the second valve being disposed within the second channel.

In some embodiments, the inflatable member is a first inflatable member, further comprising a second inflatable member.

In some embodiments, the reservoir is fluidically coupled to the pump. In some embodiments, the inflatable member is fludically coupled to the pump. In some embodiments, the inflatable member is a first inflatable member, further comprising a second inflatable member, the first inflatable member and the second inflatable member being fluidically coupled to the pump.

In some embodiments, an inflatable penile prosthesis includes an inflatable member, a reservoir configured to hold fluid, and a pump assembly. The pump assembly includes a pump, a valve body defining a first channel fluidically coupling the inflatable member and the pump and a second channel fludically coupling the reservoir and the pump, the valve body including a first valve disposed within the first channel and a second valve disposed within the second channel, and a selection member defining a lumen, the selection member being movable from a first position to a second position.

In some embodiments, the lumen of the selection member is configured to align with the first valve and the second valve when the selection member is in its first position. In some embodiments, the selection member includes a solid portion, the solid portion of the selection member is configured to align with the first valve and the second valve when the selection member is in its second position.

In some embodiments, the selection member is movably coupled to the valve body. In some embodiments, the selection member is slidably coupled to the valve body.

In some embodiments, a method for using an inflatable penile prosthesis includes moving a selection member from a first position to a second position to align a lumen defined by the selection member with a valve, and transferring fluid within a pump to an inflatable member via the valve.

In some embodiments, the moving includes moving the selection member with respect to a valve body. In some embodiments, the moving includes sliding the selection member with respect to the valve body.

DETAILED DESCRIPTION

Figure 1:
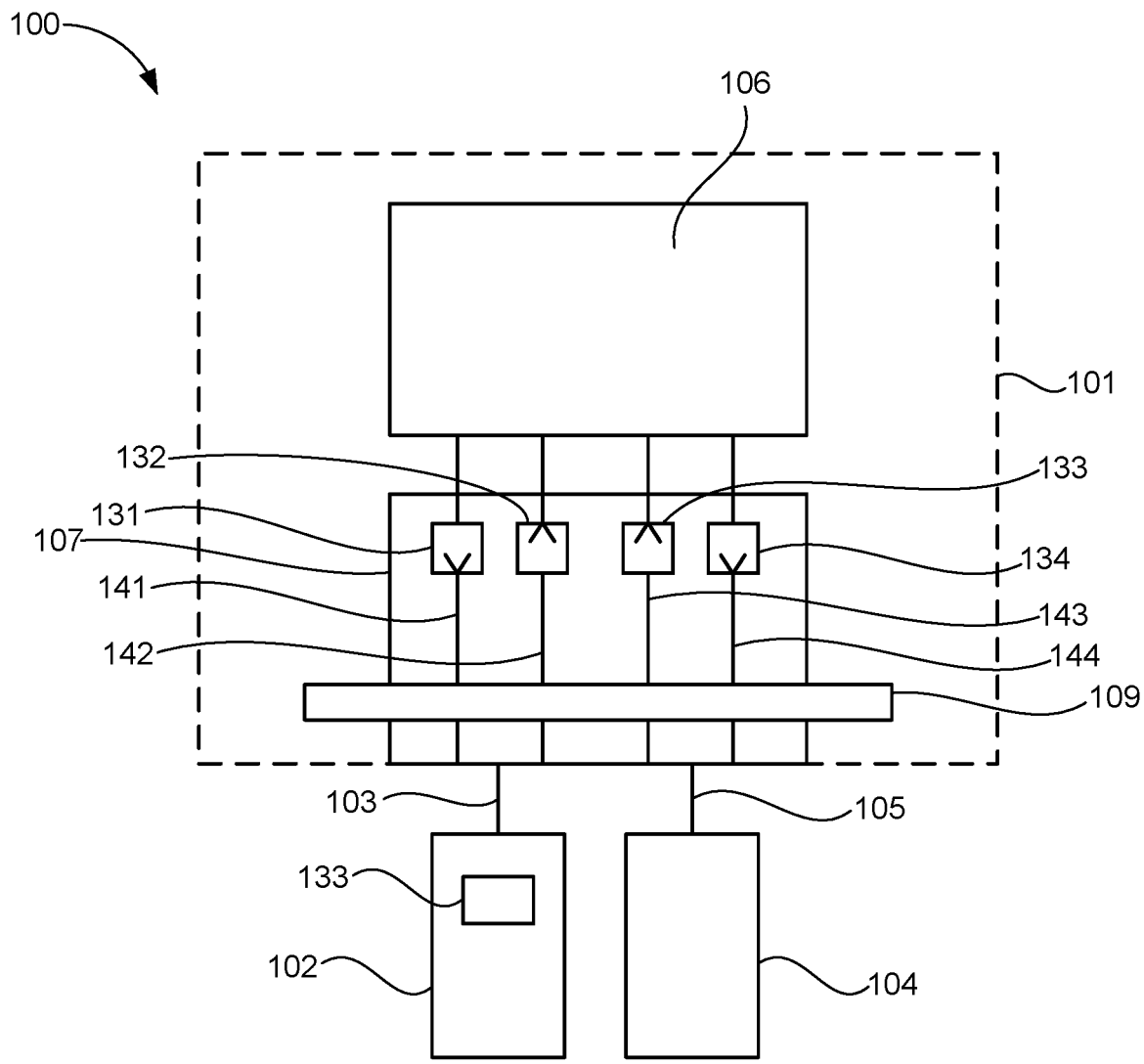
FIG. 1 schematically illustrates an inflatable penile prosthesis having a pump assembly according to an embodiment.

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are to medical devices (e.g., penile prostheses), methods of making medical devices, procedures for placing medical devices within a body of a patient, and methods for operating the medical devices. The term patient or user may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human male, a human female, or any other mammal.

The terms proximal and distal described in relation to various devices, apparatuses, and components as discussed in the subsequent text of the present disclosure are referred with a point of reference. The point of reference, as used in this description, is a perspective of a person who receives the inflatable penile prosthesis. The person may, for example, be a patient such as a male human. The term proximal refers to an area or portion that is closer or closest to the person who receives the inflatable penial prosthesis. The term distal refers to an area or portion that is farther or farthest from the person.

The embodiments discussed herein may simplify the mechanism of selecting fluidic flow orientation, thereby increasing the number of patients that could successfully operate the erect/flaccid state control interface as well as increasing the reliability of the system.

The embodiments may include an inflatable penile prosthesis having a pump assembly, an inflatable member, and a reservoir. The inflatable member may be implanted into the corpus cavernosae of a patient or user, the reservoir may be implanted in the user's abdomen or prevesical space (Retropubic space), and the pump assembly may be implanted in the scrotum. The pump assembly may switch between an inflation position and a deflation position such that a user can operate the device to place the inflatable penile prosthesis in either an inflation mode to transfer fluid from the reservoir to the inflatable member or a deflation mode to transfer the fluid from the inflatable member back to the reservoir.

The design of this inflatable penile prosthesis may reduce the number of components used for the pump assembly, thereby simplifying the overall design and functionality of the device, which may improve pump performance. For instance, one of the benefits of the reduced part count is to isolate pump performance variability by having fewer components that affect the overall functionality of the pump assembly. In some examples, the pump may be constructed from medium or low durometer material to lower the force needed to squeeze the pump (and facilitate the use of the device).

Furthermore, in some examples, metal is not used for any of the components of the pump assembly. In some examples, the components may be made or molded from a biocompatible plastic. Removing metal from the overall design may make the pump assembly MRI compatible (MR Safe Rating), which may reduce or eliminate against risks associated with long term oxidation of any metallic surfaces that could pose a potential risk to the body or the pump performance over its full life cycle.

In some examples, the reservoir may be pressurized. During use, the user may place the pump assembly to the inflation position which may cause fluid to be automatically transferred from the reservoir through the pump assembly to the inflatable member (e.g., due to pressure within the reservoir being greater than the inflatable member), which may result in the at least partial inflation of the inflatable member. Then, the user may actuate the pump bulb of the pump assembly to further transfer the fluid from the reservoir to the inflatable member, to provide the desired penis rigidity for a normal erection. In some examples, the automatic transfer to fluid to the inflatable member may cause a reduction in the amount of pumps to provide the desired penis rigidity. Also, with added pressure to the reservoir, the pump bulb can be filled at a faster rate.

When the user desires to deflate the inflatable member, the user may manually operate the selection member to the deflation position, and fluid may be automatically transferred from the inflatable member to the reservoir due to the difference in pressure between the inflatable member and the reservoir. Then, the user may squeeze the inflatable member to further deflate the inflatable member, which returns the penis to a flaccid state. Additionally, in some embodiments, when in the deflated state, the pump may be squeezed until it is placed in a collapsed position or configuration.

FIG. 1 schematically illustrates an inflatable penile prosthesis 100 according to an aspect. In some embodiments, individual components of the inflatable penile prosthesis 100 may form a seal, such as a water impermeable seal, with the adjacent components. The inflatable penile prosthesis 100 may include a reservoir 102, an inflatable member 104, and a pump assembly 101 configured to transfer fluid between the reservoir 102 and the inflatable member 104. In some examples, the inflatable member 104 may be implanted into the corpus cavernosae of the user, the reservoir 102 may be implanted in the abdomen or pelvic cavity of the user (e.g., the reservoir 102 may be implanted in the lower portion of the user's abdominal cavity or the upper portion of the user's pelvic cavity), and the pump assembly 101 may be implanted in the scrotum of the user.

The inflatable member 104 may include one or more elongate members capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of cylinders or at least two cylinders, e.g., a first cylinder member and a second cylinder member. In some examples, each cylinder may include a cylindrical silicone rubber body or sleeve which, owing to its resiliency, is expandable circumferentially and also longitudinally. The volumetric capacity of the inflatable member 104 may depend on the size of the cylinders. In some examples, the volume of fluid in each cylinder may vary from about 8 milliliters in smaller cylinders and to about 65 milliliters in larger sizes. In some examples, the first cylinder member may be larger than the second cylinder member. In other examples, the first cylinder member may have the same size as the second cylinder member. Further details of the cylinders are further explained with reference to FIGS. 2-3.

The reservoir 102 may include a container having an internal chamber configured to hold fluid that is used to inflate the inflatable member 104. The volumetric capacity of the reservoir 102 may vary depending on the size of the inflatable penile prosthesis 100. In some examples, the volumetric capacity of the reservoir 102 may be 40-50 cubic centimeters. In some examples, the reservoir 102 is constructed from the same material as the inflatable member 104. In other examples, the reservoir 102 is constructed from a different material than the inflatable member 104.

In some examples, the reservoir 102 may be pressurized. In some examples, the reservoir 102 is pressurized less than or equal to a pressurized threshold. In some examples, the reservoir 102 is pressurized to be equal to or less than diastolic pressure in order to ensure that the reservoir 102 is not over pressurized. In some examples, the pressurized threshold is 70 mm/Hg. In some examples, the pressurized threshold is greater than 70 mm/Hg. In other examples, the pressurized threshold is less than 70 mm/Hg. In some examples, the reservoir 102 includes a pressure regulating balloon. In other examples, the reservoir 102 is not pressurized (e.g., static). In some examples, reservoir 102 may include a single container configured to hold the fluid, which may or may not be pressurized. In some examples, the reservoir 102 includes a primary container (or primary chamber) and a secondary container (or secondary chamber), where the primary container/chamber may hold the fluid that is transferred to the inflatable member 104, and the secondary container/chamber may include gas or secondary fluid that is used to pressurize the fluid in the primary container/chamber.

In some examples, the reservoir 102 may include a biasing member 133 configured to pressurize the fluid in the reservoir 102. For example, upon injection of fluid into the reservoir 102, the biasing member 133 may provide a force on the fluid, thereby pressurizing the reservoir 102. The biasing member 133 may be biased to an original size or position, and the biasing member 133 may expand to a different size or position when the fluid is injected into the reservoir 102 and/or the biasing member 133, thereby creating a pressurized reservoir 102. In some examples, the biasing member 133 may include a spring or a spring-loaded assembly that biases the reservoir 102 to a particular size or position. In some examples, the biasing member 133 may be an expandable balloon inside a more rigid container of the reservoir 102. For instance, the expandable balloon may be biased to a smaller size when it is not filled with fluid. Then, upon injection of the fluid into the expandable balloon, the expandable balloon may expand and pressurize the fluid contained therein. In some examples, the biasing member 133 may be a biased diaphragm, which may be a membrane, flap, or other structure contained within the reservoir 102 that may separate one area of the reservoir 102 from another area of the reservoir 102. The diaphragm may be biased to an original position. Upon injection of the fluid into the reservoir 102, the diaphragm may flex, expand, or move to account for the increased fluid such that the fluid can be pressurized within the reservoir 102. In other examples, the reservoir 102 may be constructed from a substantially elastic walled abdominal conforming member. For example, the reservoir 102 may be located in the abdomen within the space of retzius (retropubic space) or other sub-muscular locations, and the reservoir 102 may pre-charged or pressurized (to at least two or three psi) ahead of the desired moment of transformation of the penis from flaccid to erect due to the substantially elastic walled abdominal conforming member.

The inflatable penile prosthesis 100 may include a first conduit connector 103 and a second conduit connector 105. Each of the first conduit connector 103 and the second conduit connector 105 may define a lumen configured to transfer the fluid to and from the pump assembly 101. The first conduit connector 103 may be coupled to the pump assembly 101 and the reservoir 102 such that fluid can be transferred between the pump assembly 101 and the reservoir 102 via the first conduit connector 103. For example, the first conduit connector 103 may define a first lumen configured to transfer fluid between the pump assembly 101 and the reservoir 102. The first conduit connector 103 may include a single or multiple tube members for transferring the fluid between the pump assembly 101 and the reservoir 102.

The second conduit connector 105 may be coupled to the pump assembly 101 and the inflatable member 104 such that fluid can be transferred between the pump assembly 101 and the inflatable member 104 via the second conduit connector 105. For example, the second conduit connector 105 may define a second lumen configured to transfer fluid between the pump assembly 101 and the inflatable member 104. The second conduit connector 105 may include a single or multiple tube members for transferring the fluid between the pump assembly 101 and the inflatable member 104. In some examples, the first conduit connector 103 and the second conduit connector 105 may include a silicone rubber material.

The pump assembly 101 may switch between an inflation mode in which the fluid in the reservoir 102 is transferred to the inflatable member 104 through the pump assembly 101 in a first direction (e.g., inflation direction) and a deflation mode in which the fluid in the inflatable member 104 is transferred back to the reservoir 102 through the pump assembly 101 in a second direction (e.g., deflation direction).

The pump assembly 101 may include a pump 106 and a valve body 107. The valve body 107 includes a first valve 131, a second valve 132, a third valve 133, and a fourth valve 134. Each of the valves is disposed within a fluid channel or passageway that are each fluidically coupled to the pump 106.

The valve body 107 also includes a selection member 109. The selection member 109 may be used to select or change the mode in which the pump assembly is in. For example, the selection member 109 may be moved from a first position to a second position to place the device in its deflation mode. The selection member 109 may then be moved back to its first position to place the device in its inflation mode. In some embodiments, the selection member 109 is movable with respect to the valve body 107. For example, in some embodiments, the selection member 109 is slidably coupled or slideable with respect to the valve body 107.

In some examples, metal is not used for any of the components of the pump assembly 101. In some examples, each component of the pump assembly 101 may include a polymer material. In some examples, each component of the pump assembly 101 includes a polymer material of the same type. In some examples, at least one component of the pump assembly 101 may include a non-metal material that is different from other components of the pump assembly 101. Removing metal from the overall design may provide make the pump assembly 101 MRI compatible (MRI Safe Rating), which may reduce or eliminate against risks associated with long term oxidation of any metallic surfaces that could pose a potential risk to the body or the pump performance over its full life cycle.

In the illustrated embodiment, the valves 131, 132, 133, and 134 are one-way valves. In other words, the valves 131, 132, 133, and 134 are configured to allow fluid to pass in one direction within the channel they are disposed within and are configured to help prevent or limit the fluid flow in the opposite direction. In some embodiments, the valves 131, 132, 133, and 134 are duckbill type valves. In other embodiments, the valves are another type of valve, such as a ball-check valve.

In the illustrated embodiment, valve 131 is disposed within channel 141 and is configured to allow fluid to flow from the pump 106 to the reservoir 102 via channel 141 and conduit or conduit connector 103. Valve 131 is configured to help prevent fluid from moving from the reservoir 102 to the pump 106 via channel 141. Valve 132 is disposed within channel 142 and is configured to allow fluid to flow from the reservoir 102 to the pump 106 via channel 142 and conduit 103. Valve 132 is configured to help prevent fluid from moving from the pump 106 to the reservoir 102 via channel 142. Valve 133 is disposed within channel 143 and is configured to allow fluid to flow from the inflation member 104 to the pump 106 via channel 143 and conduit 105. Valve 133 is configured to help prevent fluid from moving from the pump 106 to the inflation member 104 via channel 143. Valve 134 is disposed within channel 144 and is configured to allow fluid to flow from the pump 106 to the inflation member 104 via channel 144 and conduit 105. Valve 134 is configured to help prevent fluid from moving from the inflation member 104 to the pump 106 via channel 144.

The pump 106 may be squeezed or depressed by the user in order to facilitate the transfer of fluid from the reservoir 102 to the inflatable member 104. For example, in the inflation mode, while the user is operating the pump 106, the pump 106 may receive the fluid from the reservoir 102, and then output the fluid to the inflatable member 104. When the user switches to the deflation mode, at least some of the fluid can automatically be transferred back to the reservoir 102 (due to the difference in pressure from the inflatable member 104 to the reservoir 102). Then, the user may squeeze the inflatable member 104 to facilitate the further transfer of fluid through the pump 106 to the reservoir 102.

In some examples, the pump 106 may include a flexible member defining a cavity. In some examples, the pump 106 may define a pump shell having a flexible bulb and a valve body connector, where the valve body connector is designed to fit at least partially over the valve body 107. In some examples, the pump 106 may include a squeeze pump. In some examples, the pump 106 may include a portion that is round or substantially round. In some examples, the pump 106 may include ribbing or dimples to aid the user in gripping the pump 106. The pump 106 may use suction and pressure to move the fluid in and out of the cavity of the pump 106 in the inflation mode. For example, the user may depress or squeeze the pump 106 to expel the fluid out of the cavity, and, when the flexible member returns to its original shape, the resulting suction pulls the fluid into the cavity of the pump 106. In some examples, the pump 106 may have a bulb spring rate that is designed to refill the pump 106 in a selected time frame. In some examples, the bulb spring rate (especially in the completely flattened state of the squeezed pump bulb) may be selectively enhanced to create a vacuum by the addition of a nitinol spring configured as a sphere that exerts opening force on the bulb walls. This spring could also be designed such that it does not substantially increase the compressive squeeze force required to expel fluid out of the bulb in the opened state through the use of hinge/buckle points.

As discussed above, the selection member 109 may be used to select or change the mode in which the pump assembly is in. In some embodiments, the selection member 109 includes or defines at least one opening, hole, or lumen. The selection member 109 is configured to be moved from one position in which it allows fluid to flow through one or more of the channels and another position in which it allows fluid to flow though a different or a different set of channels. For example, in one embodiment, the selection member 109 may be placed in the inflate position (for example, such that openings align with the channel 142 and valve 132 and channel 144 and valve 134 and so that a solid portion of the selection member 109 effectively blocks channel 141 and valve 131 and channel 143 and valve 133). The user may then operate the pump 106 to inflate the inflatable member 104 (i.e., move the fluid from the reservoir 102 to the inflatable member 104). For example, the user may repeatedly depress or squeeze the pump 106 until the desired rigidity is achieved. For example, squeezing the pump 106 may force fluid through valve 134. The pump 106 may then return to its original form, which provides a suction force causing fluid to be drawn into the pump 106 from the reservoir via valve 132. The flow from the reservoir 102 fills the pump 106 (or at least partially fills the pump 106) until the pump's pressure is substantially equal to the reservoir's pressure. This pump cycle is repeated until the desired rigidity in the inflatable member 104 is achieved.

In some examples, if the reservoir 102 is at least partially pressurized, the fluid may automatically flow out of the reservoir 102 and into the inflatable member 104 without the user depressing or squeezing the pump 106 until the pressure is at least partially equalized between the reservoir 102 and the inflatable member 104.

Then, when the user wants to deflate the inflatable member 104, the user moves selection member 109 to its deflate position. For example, in this position, openings of the selection member 109 align with the channel 141 and valve 131 and channel 143 and valve 133 and a solid portion of the selection member 109 effectively blocks channel 142 and valve 132 and channel 144 and valve 134). The user may then operate the pump 106 to deflate the inflatable member 104 (i.e., move the fluid from the inflatable member 104 to the reservoir 102). For example, the user may repeatedly depress or squeeze the pump 106 until the deflation is completed. For example, squeezing the pump 106 may force fluid through valve 131. The pump 106 may then return to its original form, which provides a suction force causing fluid to be drawn into the pump 106 from the inflation member 104. The fluid from the inflation member 104 fills the pump 106 (or at least partially fills the pump 106). This pump cycle is repeated until the inflatable member 104 is deflated.

In some examples, the fluid may automatically (upon movement of the selection member 109 to its deflate position) flow out of the inflatable member 104 and into the reservoir 102 without the user depressing or squeezing the pump 106 until the pressure is at least partially equalized between the reservoir 102 and the inflatable member 104.

In some examples, after the inflation member 104 has been deflated, the pump 106 may be squeezed to place the pump in a contracted position or configuration.

As indicated above, the design of this inflatable penile prosthesis 100 may reduce the number of components used for the pump assembly 101, thereby simplifying the overall design and functionality of the device, which may improve pump performance.

Figure 2:
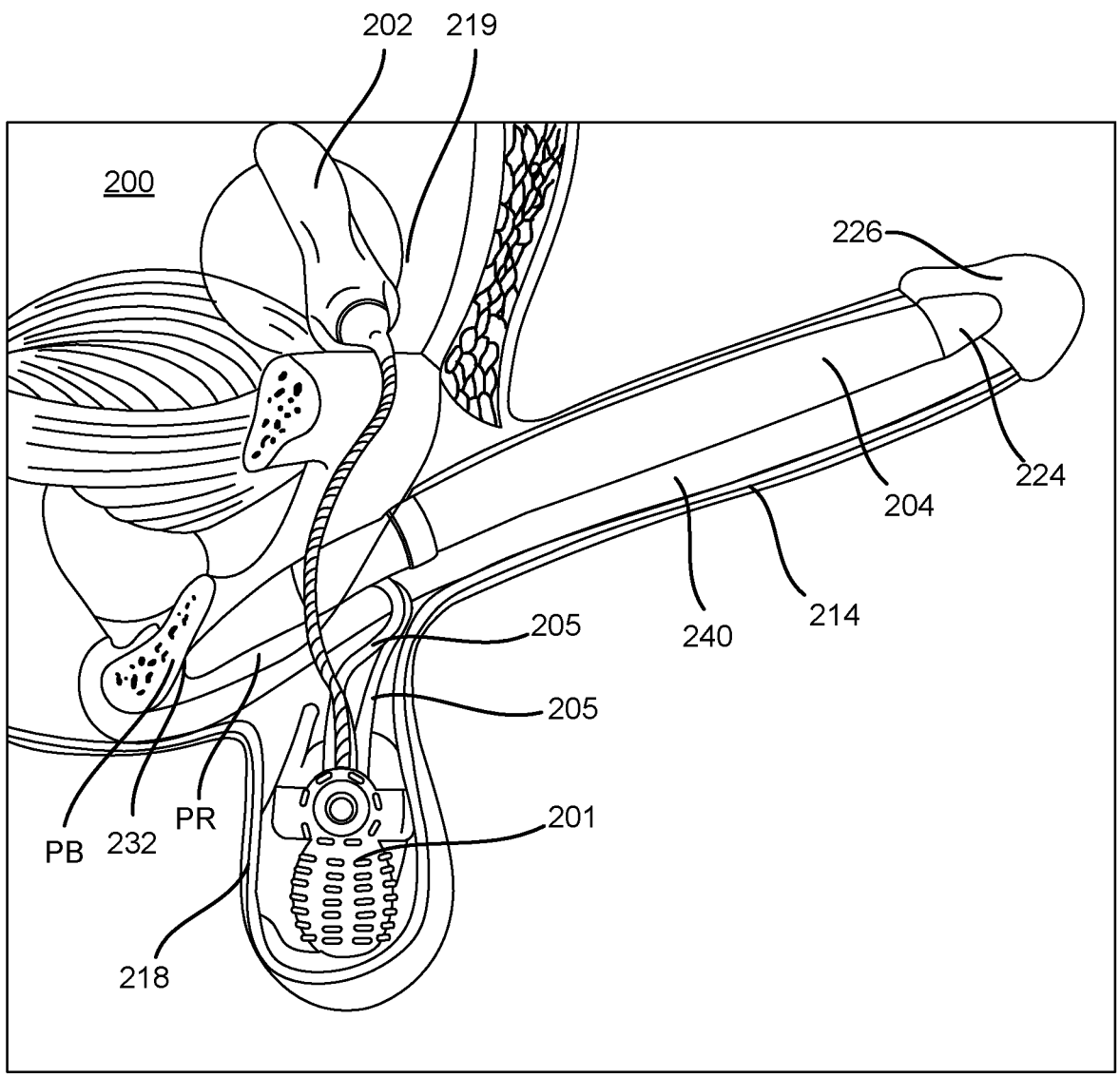
FIG. 2 illustrates an inflatable penile prosthesis implanted within a patient according to an embodiment.
Figure 3:
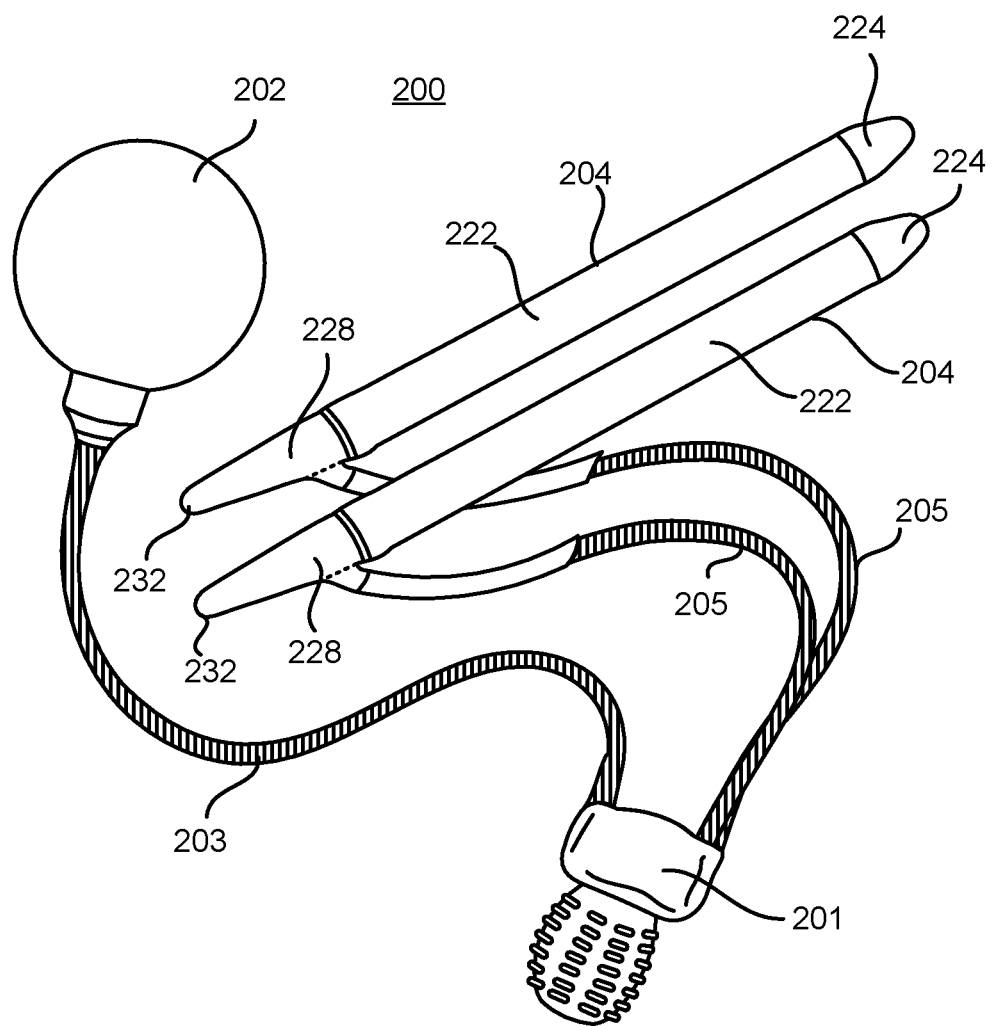
FIG. 3 is a perspective view of the inflatable penile prosthesis of FIG. 2.

FIG. 2 illustrates an inflatable penile prosthesis 200 implanted within a user according to an aspect. FIG. 3 illustrates the inflatable penile prosthesis 200.

Referring to FIGS. 2-3, the inflatable penile prosthesis 200 may include a pair of cylinders 204, and the pair of cylinders 204 are implanted in a penis 214. For example, one of the cylinders 204 may be disposed on one side of the penis 214. The other cylinder 204 (not shown in FIG. 2) of the pair of cylinders may be disposed on the other side of the penis 214. The cylinder 204 may include a distal end portion 224, an inflation chamber 222, and a proximal end portion 228 having a rear tip 232.

The inflatable penile prosthesis 200 may include a pump assembly 201, which may be implanted into the patient's scrotum 218. The pump assembly 201 may include any of the features discussed with reference to the reversible flow pump assembly of any of the figures. A pair of conduit connectors 205 may attach the pump assembly 201 to the pair of cylinders 204 such that the pump assembly 201 is in fluid communication with the pair of cylinders 204. Also, the pump assembly 201 may be in fluid communication with a reservoir 202 via a conduit connector 203, where the reservoir 202 that may be implanted into the user's abdomen 219. The inflation chamber 222 of the cylinder 204 may be disposed within the penis 214. The distal end portion 224 of the cylinder 204 may be at least partially disposed within the crown portion 226 of the penis 214. The proximal end portion 228 may be implanted into the patient's pubic region PR with the rear tip 232 proximate the pubic bone PB.

In order to implant the cylinder 204, the surgeon first prepares the patient. The surgeon often makes an incision in the penoscrotal region, e.g., where the base of the penis 214 meets with the top of the scrotum 218. From the penoscrotal incision, the surgeon may dilate the patient's corpus cavernosae 240 to prepare the patient to receive the pair of cylinders 204. The corpus cavernosum is one of two parallel columns of erectile tissue forming the dorsal part of the body of the penis 214, e.g., two slender columns that extend substantially the length of the penis 214. The surgeon will also dilate two regions of the pubic area (proximal corpora cavernosae) to prepare the patient to receive the proximal end portion 228. The surgeon may measure the length of the proximal and distal corpora cavernosae from the incision and the dilated region of the pubic area to determine an appropriate size of the cylinder 204 to implant.

After the patient is prepared, the inflatable penile prosthesis 200 is implanted into the patient. The distal tip of the distal end portion 224 of each cylinder 204 may be attached to a suture. The other end of the suture may be attached to a needle member (e.g., Keith needle). The needle member is inserted into the incision and into the dilated corpus cavernosum. The needle member is then forced through the crown of the penis 214. The surgeon tugs on the suture to pull the cylinder 204 into the corpus cavernosum. This is done for each cylinder of the pair of cylinders 204. Once the inflation chamber 222 is in place, the surgeon may remove the suture from the distal tip. The surgeon then inserts the proximal end portion 228. The surgeon inserts the rear end of the cylinder 204 into the incision and forces the proximal end portion 228 toward the pubic bone PB until each cylinder 204 is in place.

Figure 4:
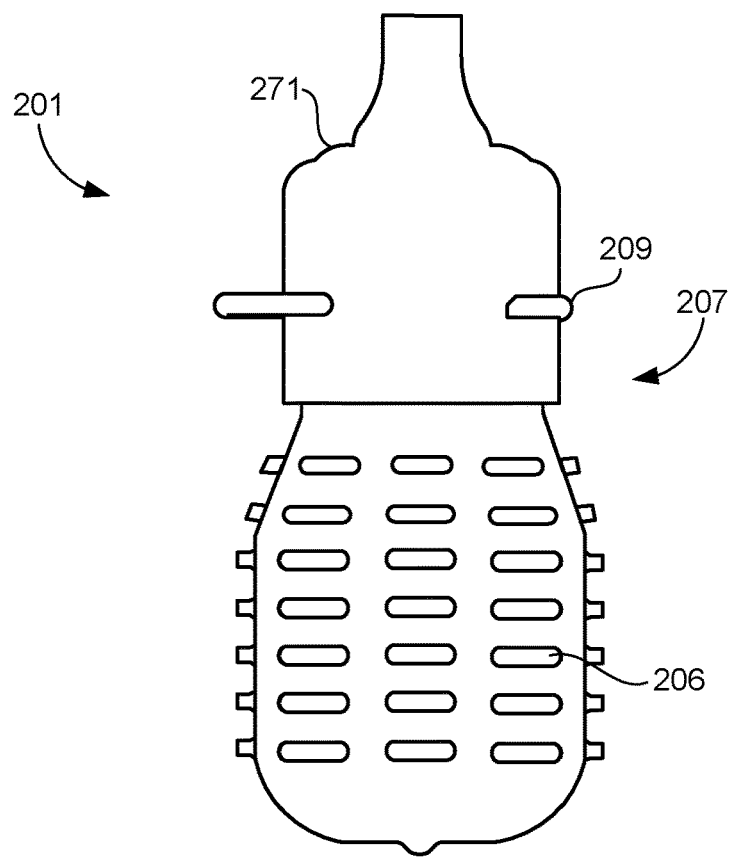
FIG. 4 is a side view of a pump assembly of the inflatable penile prosthesis of FIG. 2.
Figure 5:
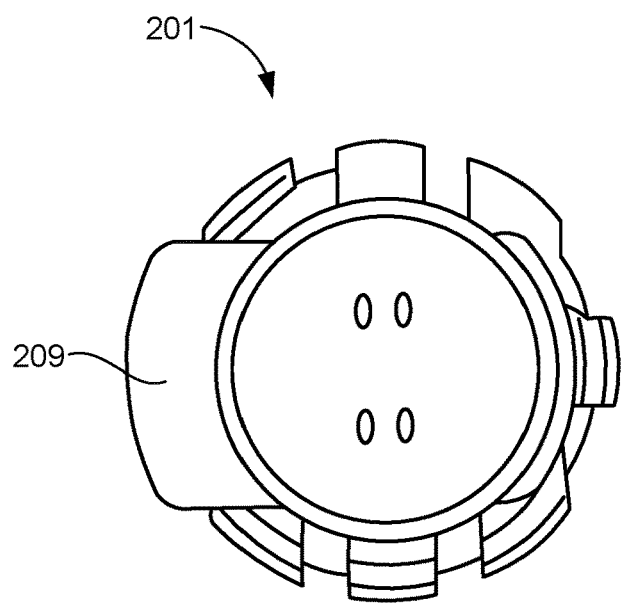
FIG. 5 is a end view of the pump assembly of FIG. 4
Figure 6:
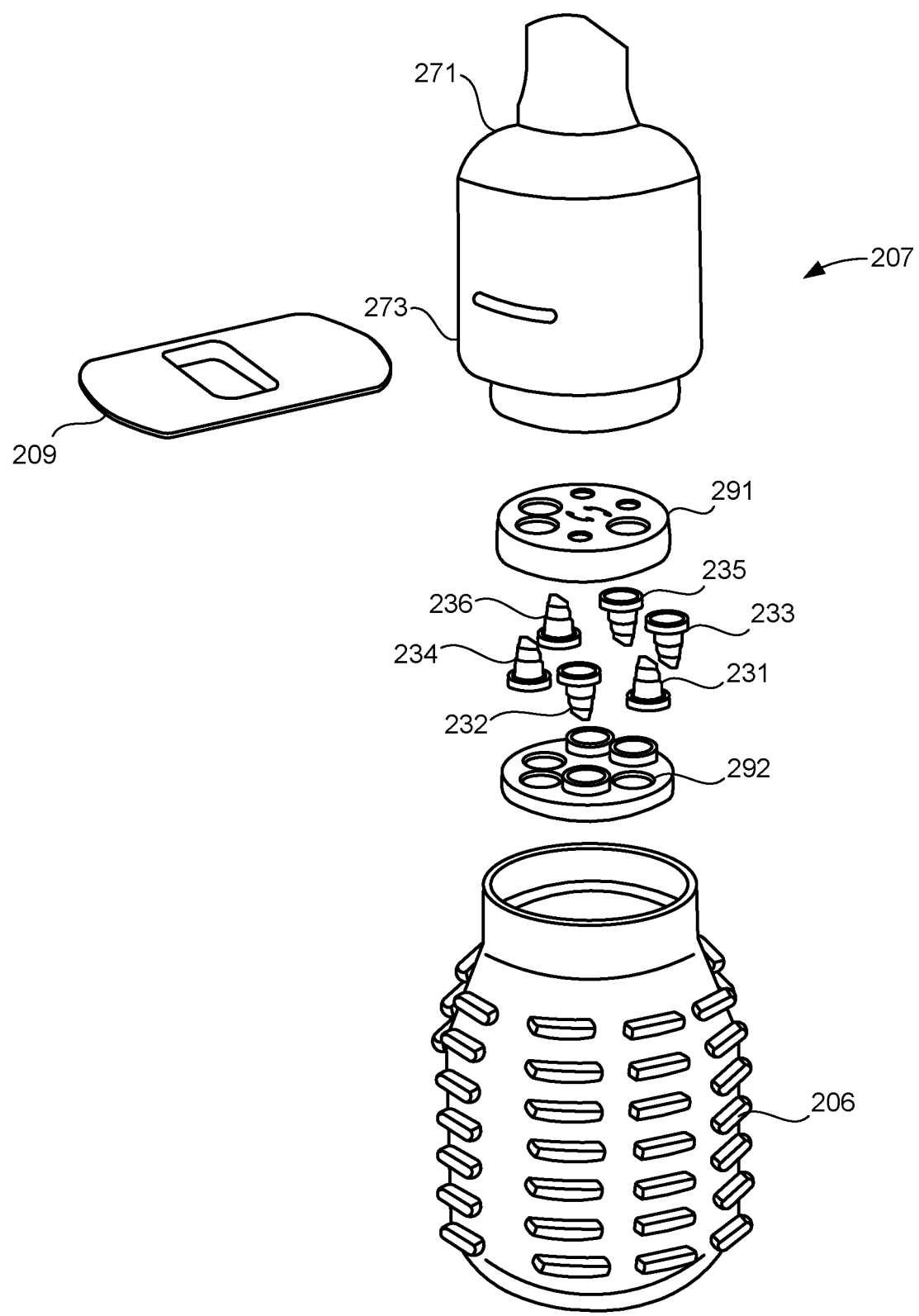
FIG. 6 is an exploded view of the pump assembly of FIG. 4.

FIG. 4 is a side view of the pump assembly 201. FIG. 5 is an end view of the pump assembly 201 and FIG. 6 is an exploded view of the pump assembly 201.

The pump assembly 201 may switch between an inflation mode in which the fluid in the reservoir 202 is transferred to the inflatable member 204 (or inflatable members) through the pump assembly 201 in a first direction (e.g., inflation direction) and a deflation mode in which the fluid in the inflatable member 204 (or inflatable members) is transferred back to the reservoir 202 through the pump assembly 201 in a second direction (e.g., deflation direction).

The pump assembly 201 includes a pump (or pump bulb) 206 and a valve body 207, and a selection member 209. The valve body 207 includes an upper member 291, a lower member 292, and valves 231, 232, 233, 234, 235, and 236. Each of the valves is disposed within a fluid channel or passageway that are each fluidically coupled to the pump 206.

Figure 7:
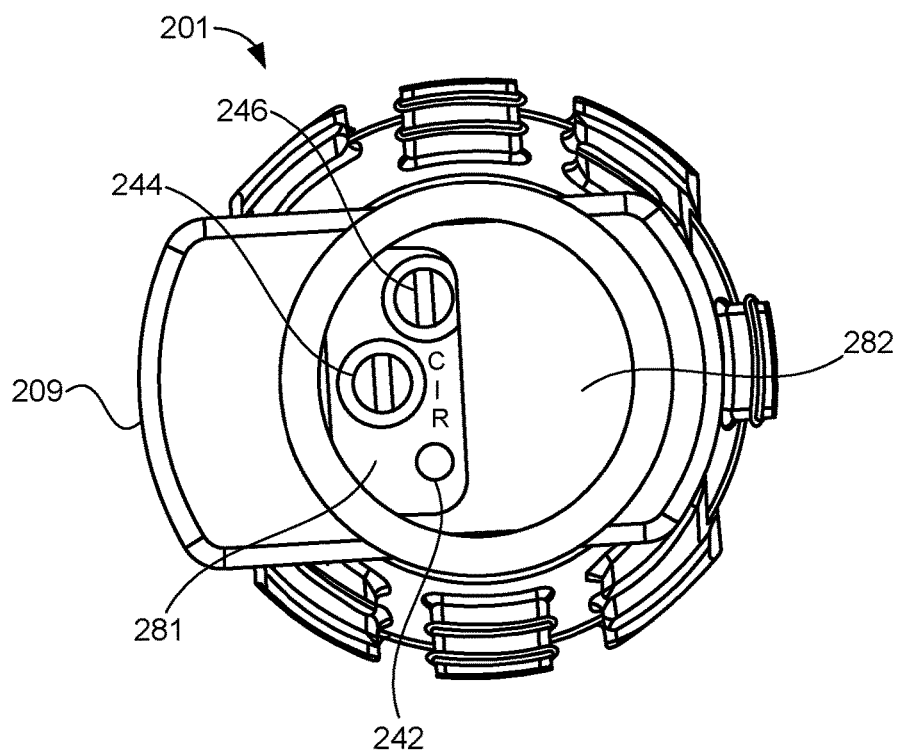
FIG. 7 is a top view of a portion of the pump assembly of FIG. 4 in a first configuration.
Figure 8:
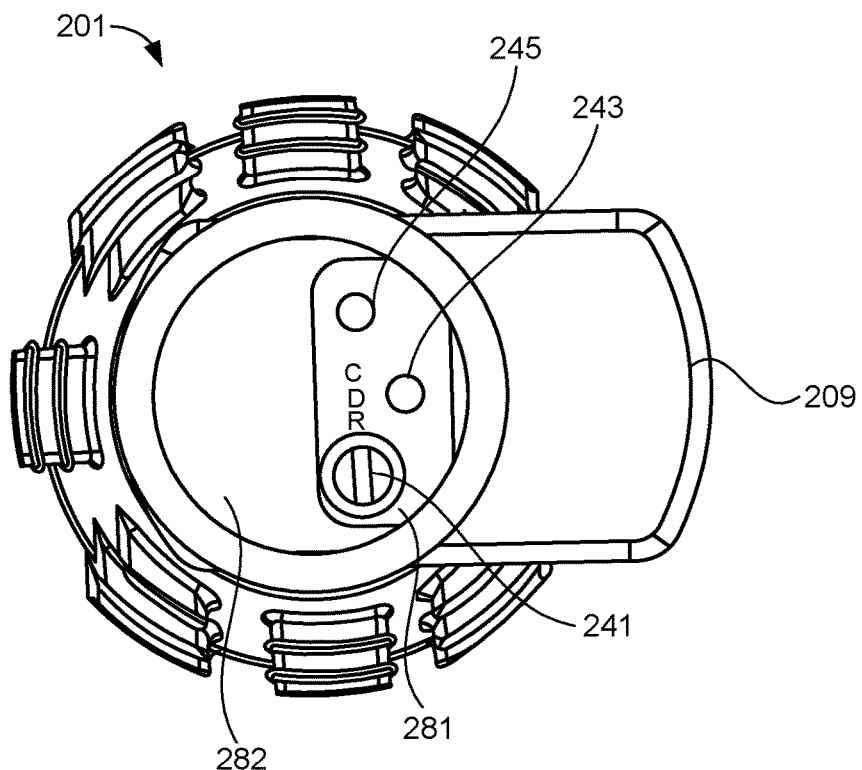
FIG. 8 is a top view of a portion of the pump assembly of FIG. 4 in a second configuration.
Figure 9:
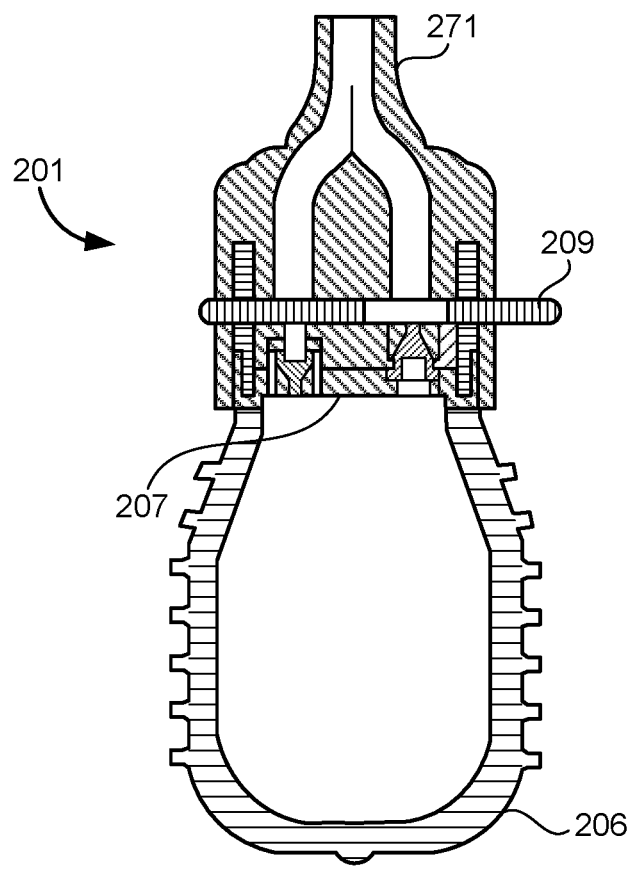
FIG. 9 is a cross-sectional view of the pump assembly of FIG. 4.
Figure 10:
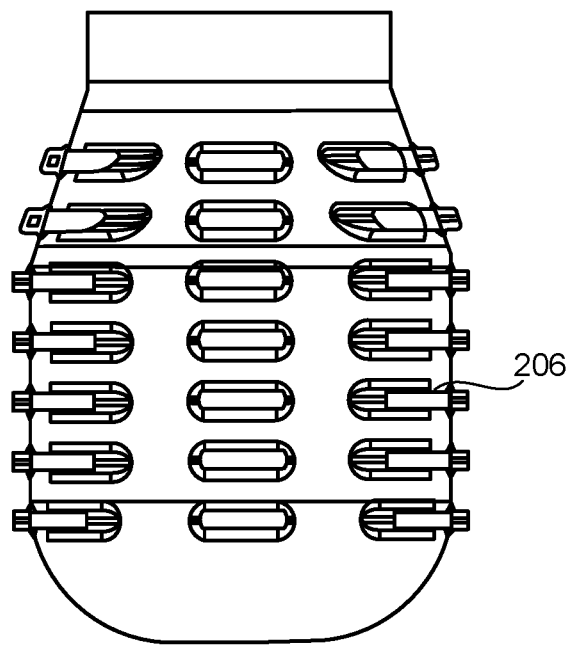
FIG. 10 is a side view of a pump of the pump assembly of FIG. 4.
Figure 11:
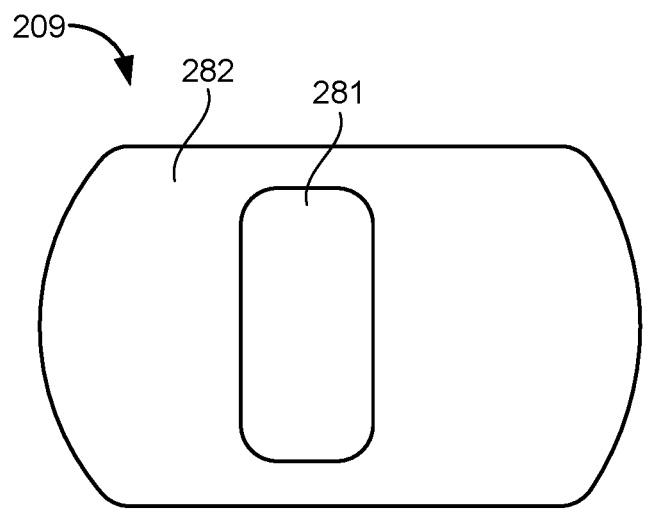
FIG. 11 is top view of a selection member of the pump assembly of FIG. 4.
Figure 12:
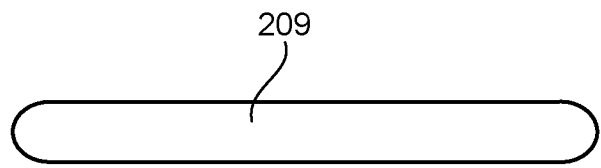
FIG. 12 is a side view of the selection member of FIG. 11.

The selection member 209 may be used to select or change the mode in which the pump assembly 201 is in. For example, the selection member 209 may be moved from a first position to a second position to place the device in its deflation mode. FIG. 8 illustrates the selection member 209 in its second position (the deflation mode). The selection member 209 may then be moved back to its first position to place the device in its inflation mode. FIG. 7 illustrates the selection member 209 in its first position (the inflation mode). In some embodiments, the selection member 209 is movable with respect to the valve body 207. For example, in the illustrated embodiment, the selection member 209 is slidably coupled or slideable with respect to the valve body 207. In some embodiments, the selection member 209 includes stop members, such as shoulders or detents that engage members of the valve body 207 to lock or help retain the selection member 209 in one of its first and second positions.

In some examples, metal is not used for any of the components of the pump assembly 201. In some examples, each component of the pump assembly 201 may include a polymer material. In some examples, each component of the pump assembly 201 includes a polymer material of the same type. In some embodiments, the components of the pump assembly 201 are made of silicone or acrylonitrile butadiene styrene (ABS). In some examples, at least one component of the pump assembly 201 may include a non-metal material that is different from other components of the pump assembly 201. Removing metal from the overall design may provide make the pump assembly 201 MRI compatible (MRI Safe Rating), which may reduce or eliminate against risks associated with long term oxidation of any metallic surfaces that could pose a potential risk to the body or the pump performance over its full life cycle.

In the illustrated embodiment, the valves 231, 232, 233, 234, 235, and 236 are one-way valves. In other words, the valves 231, 232, 233, 234, 235, and 236 are configured to allow fluid to pass in one direction within the channel they are disposed within and are configured to help prevent or limit the fluid flow in the opposite direction. In the illustrated embodiment, the valves 231, 232, 233, 234, 235, and 236 are duckbill type valves. In other embodiments, the valves are another type of valve, such as a ball-check valve.

Figure 13:
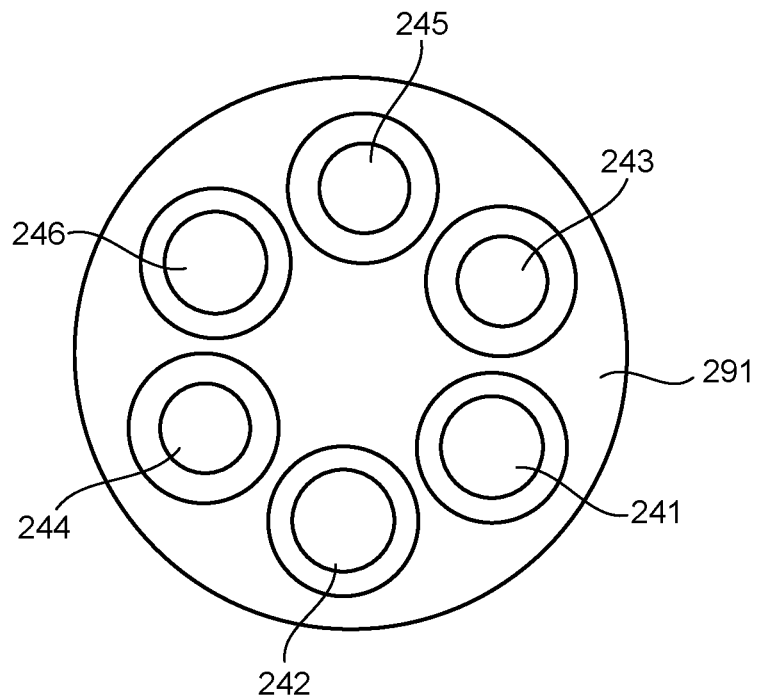
FIG. 13 is a top view of a lower member of a valve body.
Figure 14:
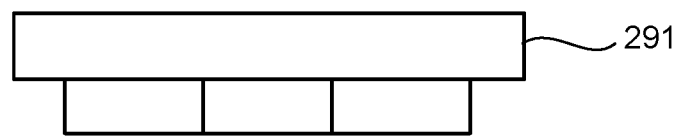
FIG. 14 is a side view of a lower member of FIG. 13.
Figure 15:
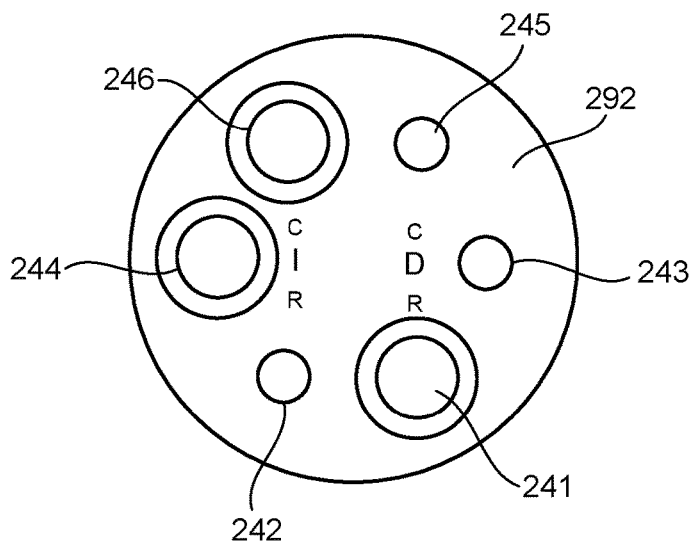
FIG. 15 is a top view of an upper member of the valve body.
Figure 16:
FIG. 16 is a side view of the upper member of FIG. 15.
Figure 17:
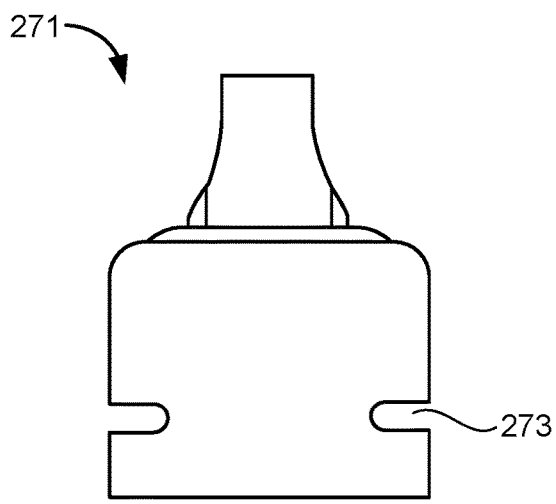
FIG. 17 is a side view of an adaptor of the pump assembly of FIG. 4.

In the illustrated embodiment, the valve body 207 defines a plurality of channels that facilitate the movement of fluid from the pump 206 to the reservoir 202 and to the inflatable members 204. One of the valves is disposed within each of the channels or fluid pathways. As best illustrated in FIGS. 13 and 15, the channels or fluid pathways of the valve body 207 are at least partially defined by the upper member 291 and the lower member 292 of the valve body 207.

In the illustrated embodiment, valve 231 is disposed within channel 241 and is configured to allow fluid to flow from the pump 206 to the reservoir 202 via channel 241 and the conduit 203. Valve 231 is configured to help prevent fluid from moving from the reservoir 202 to the pump 206 via channel 241. Valve 232 is disposed within channel 242 and is configured to allow fluid to flow from the reservoir 202 to the pump 206 via channel 242 and the conduit 203. Valve 232 is configured to help prevent fluid from moving from the pump 206 to the reservoir 202 via channel 242.

Valve 233 is disposed within channel 243 and is configured to allow fluid to flow from one of the inflation members 204 to the pump 206 via channel 243 and one of the conduits 205. Valve 233 is configured to help prevent fluid from moving from the pump 206 to the inflation member 204 via channel 243. Valve 234 is disposed within channel 244 and is configured to allow fluid to flow from the pump 206 to the inflation member 204 via channel 244 and the conduit member 205. Valve 234 is configured to help prevent fluid from moving from the inflation member 204 to the pump 206 via channel 244.

Valve 235 is disposed within channel 245 and is configured to allow fluid to flow from one of the inflation members 204 to the pump 206 via channel 245 and one of the conduits 205. Valve 235 is configured to help prevent fluid from moving from the pump 206 to the inflation member 204 via channel 245. Valve 236 is disposed within channel 246 and is configured to allow fluid to flow from the pump 206 to the inflation member or cylinder 204 via channel 246 and the conduit member 205. Valve 236 is configured to help prevent fluid from moving from the inflation member 204 to the pump 206 via channel 246.

The pump 206 may be squeezed or depressed by the user in order to facilitate the transfer of fluid from the reservoir 202 to the inflatable member 204. For example, in the inflation mode, while the user is operating the pump 206, the pump 206 may receive the fluid from the reservoir 202, and then output the fluid to the inflatable member 204. When the user switches to the deflation mode, at least some of the fluid can automatically be transferred back to the reservoir 202 (due to the difference in pressure from the inflatable member 204 to the reservoir 202). Then, the user may squeeze the inflatable member 204 to facilitate the further transfer of fluid through the pump 206 to the reservoir 202.

In the illustrated embodiment, the pump 206 includes a flexible member defining a cavity. In some examples, the pump 106 may include a squeeze pump.

As discussed above, the selection member 209 may be used to select or change the mode in which the pump assembly is in. In the illustrated embodiment, the selection member 209 includes or defines an opening, hole, or lumen 281. The selection member 209 also includes a substantially solid portion 282. In the illustrated embodiment, the substantially solid portion 282 is fluid impermeable (fluid cannot pass through the substantially solid portion 282). The selection member 209 is configured to be moved from one position in which it allows fluid to flow through one or more of the channels and another position in which it allows fluid to flow through a different or a different set of channels.

As illustrated in FIG. 7, the selection member 209 may be placed in the inflate position. In the inflate position the opening 281 of the selection member 209 aligns with the channel 242, 244, and 246 and valves 232, 234, and 236 and so that the solid portion 282 of the selection member 209 effectively blocks channels 241, 243, and 245 and valves 231, 233, and 235. The user may then operate the pump 206 to inflate the inflatable members 204 (i.e., move the fluid from the reservoir 202 to the inflatable member 204). For example, the user may repeatedly depress or squeeze the pump 206 until the desired rigidity is achieved. For example, squeezing the pump 206 may force fluid through valves 234 and 236. The pump 206 may then return to its original form, which provides a suction force causing fluid to be drawn into the pump 206 from the reservoir via valve 232. The flow from the reservoir 202 fills the pump 206 (or at least partially fills the pump 206) until the pump's pressure is substantially equal to the reservoir's pressure. This pump cycle is repeated until the desired rigidity in the inflatable members 204 is achieved.

In some examples, if the reservoir 202 is at least partially pressurized, the fluid may automatically flow out of the reservoir 202 and into the inflatable member 204 without the user depressing or squeezing the pump 206 until the pressure is at least partially equalized between the reservoir 202 and the inflatable member 204.

Then, when the user wants to deflate the inflatable members 204, the user moves selection member 209 to its deflate position. As illustrated in FIG. 8, in this position, opening 281 of the selection member 209 aligns with the channels 241, 243, and 245 and valves 231, 233, and 235 and the solid portion 282 of the selection member 209 effectively blocks channels 242, 244, and 246 and valves 232, 234, and 236. The user may then operate the pump 206 to deflate the inflatable members 204 (i.e., move the fluid from the inflatable members 204 to the reservoir 202). For example, the user may repeatedly depress or squeeze the pump 206 until the deflation is completed. For example, squeezing the pump 206 may force fluid through valve 231. The pump 206 may then return to its original form, which provides a suction force causing fluid to be drawn into the pump 206 from the inflation members 204. The fluid from the inflation members 104 fills the pump 206 (or at least partially fills the pump 206). This pump cycle is repeated until the inflatable members 204 are deflated.

In some examples, the fluid may automatically (upon movement of the selection member 209 to its deflate position) flow out of the inflatable member 204 and into the reservoir 202 without the user depressing or squeezing the pump 206 until the pressure is at least partially equalized between the reservoir 202 and the inflatable member 204.

In some examples, after the inflation member 204 has been deflated, the pump 206 may be squeezed to place the pump in a contracted position or configuration.

As indicated above, the design of this inflatable penile prosthesis 200 may reduce the number of components used for the pump assembly 201, thereby simplifying the overall design and functionality of the device, which may improve pump performance.

Figure 18:
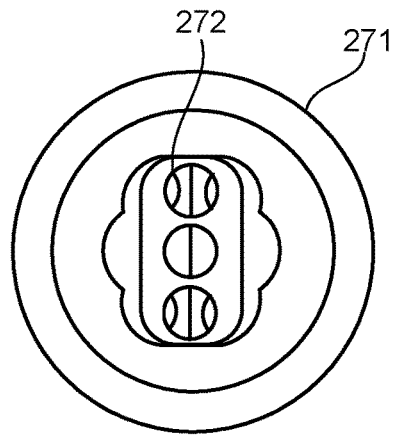
FIG. 18 is a top view of the adaptor of FIG. 17.
Figure 19:
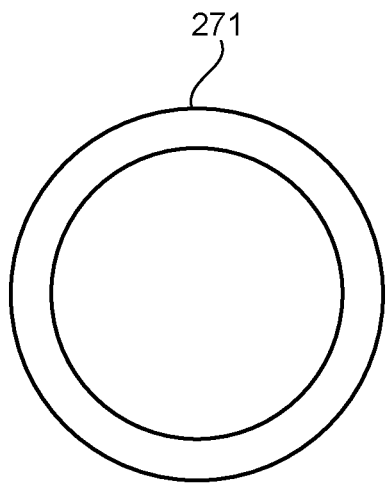
FIG. 19 is a bottom view of the adaptor of FIG. 17.
Figure 20:
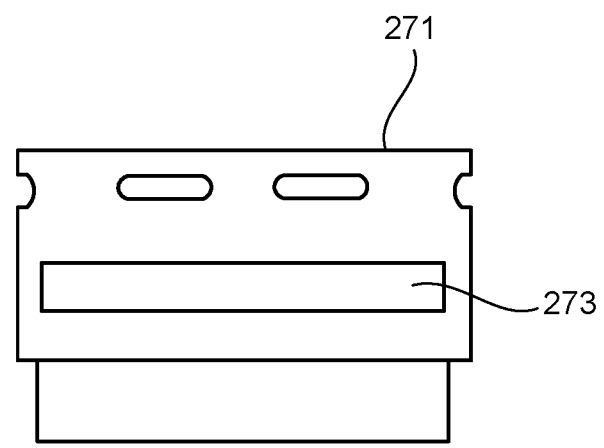
FIG. 20 is a side view of a portion of the adaptor of FIG. 17.

In the illustrated embodiment, the pump assembly 201 includes an adaptor 271. The adaptor 271 is disposed between the pump 206 and the reservoir 202 and the inflation member 204. The adaptor 271 is configured to facilitate or be coupled to the conduits 203 and 205 which fluidically couple the reservoir 202 to the pump 206 and the inflation member 204 and the pump 206. As best illustrated in FIG. 18, the adaptor 271 includes a coupling portion 272 that is configured to be coupled to the conduits 203 and 205. The adaptor 271 defines a slot or opening 273. The slot or opening 273 is configured to receive the selection member 209. Specifically, the selection member 209 is configured to slide or move within the slot or opening 273.

FIGS. 21-24 illustrate a pump assembly 301 according to an embodiment. In some embodiments, individual components of the pump assembly 301 may form a seal, such as a water impermeable seal, with the adjacent components. RES identifies the conduit or pathway that leads from the pump assembly 301 to the reservoir. CYLs identifies the conduit or pathway that leads from the pump assembly 301 to the cylinders or inflation members.

The pump assembly 301 may switch between an inflation mode in which the fluid in the reservoir is transferred to the inflatable member (or inflatable members) through the pump assembly 301 in a first direction (e.g., inflation direction) and a deflation mode in which the fluid in the inflatable member (or inflatable members) is transferred back to the reservoir through the pump assembly 301 in a second direction (e.g., deflation direction).

The pump assembly 301 includes a pump 306 and a valve body 307, and a selection member 309. The valve body 307 valves 331, 332, 333, and 334. Each of the valves is disposed within a fluid channel or passageway that are each fluidically coupled to the pump 306.

Figure 21:
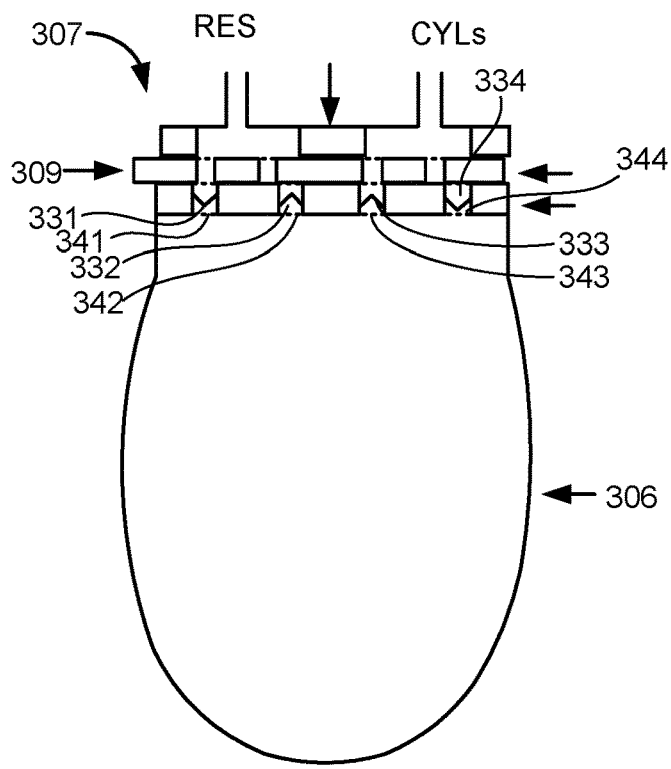
FIG. 21 is a side view of a pump assembly in a first configuration according to an embodiment.
Figure 22:
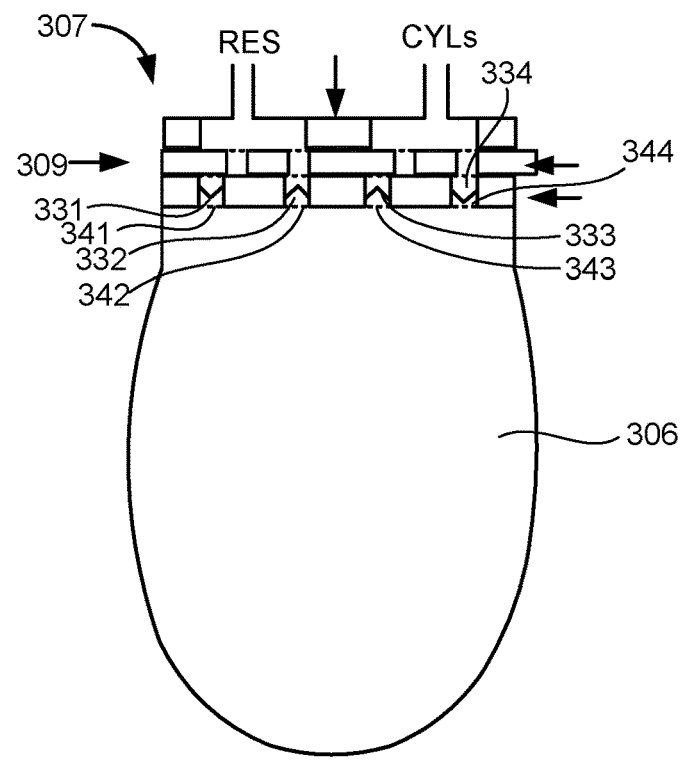
FIG. 22 is a side view of the pump assembly of FIG. 21 in a second configuration.
Figure 23:
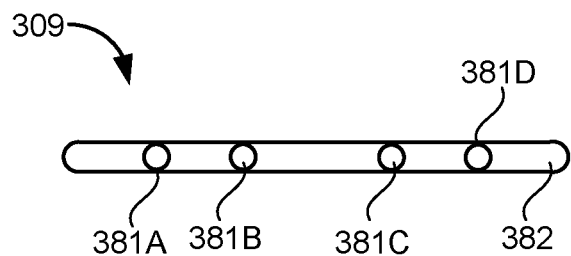
FIG. 23 is a top view of a selection member of the pump assembly of FIG. 21.

The selection member 309 may be used to select or change the mode in which the pump assembly 301 is in. For example, the selection member 309 may be moved from a first position to a second position to place the device in its deflation mode. FIG. 22 illustrates the selection member 309 in its second position (the deflation mode). The selection member 309 may then be moved back to its first position to place the device in its inflation mode. FIG. 21 illustrates the selection member 309 in its first position (the inflation mode). In some embodiments, the selection member 309 is movable with respect to the valve body 307. For example, in the illustrated embodiment, the selection member 309 is slidably coupled or slideable with respect to the valve body 307.

Figure 24:
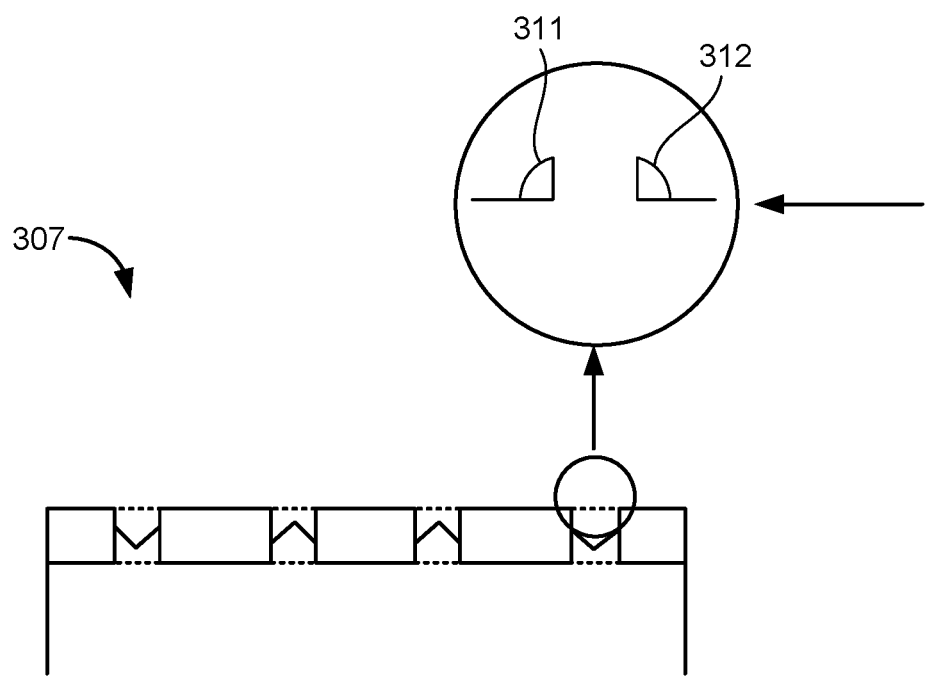
FIG. 24 is a side view of a portion of the pump assembly of FIG. 21.

As best illustrated in FIG. 24, the valve body 307 includes or defines stop members 311 and 312. The stop members 311 and 312 are configured to contact or engage the selection member 309 to help stop or lock the selection member 309 in one of its first and second positions. Accordingly, a user can move the selection member 309 and stop or lock the selection member in one of its first or second positions.

In the illustrated embodiment, the valves 331, 332, 333, and 334 are one-way valves. In other words, the valves 331, 332, 333, and 334 are configured to allow fluid to pass in one direction within the channel they are disposed within and are configured to help prevent or limit the fluid flow in the opposite direction.

In the illustrated embodiment, the valve body 307 defines a plurality of channels that facilitate the movement of fluid from the pump 306 to the reservoir and to the inflatable member. One of the valves is disposed within each of the channels or fluid pathways.

In the illustrated embodiment, valve 332 is disposed within channel 342 and is configured to allow fluid to flow from the pump 306 to the reservoir via channel 342. Valve 332 is configured to help prevent fluid from moving from the reservoir to the pump 306. Valve 331 is disposed within channel 341 and is configured to allow fluid to flow from the reservoir to the pump 306 via channel 341. Valve 331 is configured to help prevent fluid from moving from the pump 306 to the reservoir via channel 341.

Valve 334 is disposed within channel 344 and is configured to allow fluid to flow from the inflation members to the pump 306 via channel 344. Valve 334 is configured to help prevent fluid from moving from the pump 306 to the inflation member via channel 344. Valve 333 is disposed within channel 343 and is configured to allow fluid to flow from the pump 306 to the inflation member via channel 343. Valve 333 is configured to help prevent fluid from moving from the inflation member to the pump 306 via channel 343.

The pump 306 may be squeezed or depressed by the user in order to facilitate the transfer of fluid from the reservoir to the inflatable member. For example, in the inflation mode, while the user is operating the pump 306, the pump 306 may receive the fluid from the reservoir, and then output the fluid to the inflatable member. When the user switches to the deflation mode, at least some of the fluid can automatically be transferred back to the reservoir (due to the difference in pressure from the inflatable member to the reservoir). Then, the user may squeeze the inflatable member to facilitate the further transfer of fluid through the pump 306 to the reservoir.

As discussed above, the selection member 309 may be used to select or change the mode in which the pump assembly is in. In the illustrated embodiment, the selection member 309 includes or defines openings, holes, or lumens 381A, 381B, 381C, and 381D. The selection member 309 also includes a substantially solid portion 382. In the illustrated embodiment, the substantially solid portion 382 is fluid impermeable (fluid cannot bass through the substantially solid portion 382). The selection member 309 is configured to be moved from one position in which it allows fluid to flow through one or more of the channels and another position in which it allows fluid to flow though a different or a different set of channels.

As illustrated in FIG. 21, the selection member 309 may be placed in the inflate position. In the inflate position openings of the selection member 309 align with channels 341 and 343 and valves 331 and 333. Additionally, the solid portion 382 of the selection member 309 effectively blocks channels 342 and 344 and valves 332 and 334. The user may then operate the pump 306 to inflate the inflatable members (i.e., move the fluid from the reservoir to the inflatable member). For example, the user may repeatedly depress or squeeze the pump 306 until the desired rigidity is achieved. For example, squeezing the pump 306 may force fluid through valve 333. The pump 306 may then return to its original form, which provides a suction force causing fluid to be drawn into the pump 306 from the reservoir via valve 331. The flow from the reservoir fills the pump 306 (or at least partially fills the pump 306) until the pump's pressure is substantially equal to the reservoir's pressure. This pump cycle is repeated until the desired rigidity in the inflatable member is achieved.

Then, when the user wants to deflate the inflatable member, the user moves selection member 309 to its deflate position. As illustrated in FIG. 22, in this position, openings of the selection member 309 align with the channels 342 and 344 and valves 332 and 334. Additionally, the solid portion 382 of the selection member 309 effectively blocks channels 341 and 343 and valves 331 and 333. The user may then operate the pump 306 to deflate the inflatable members (i.e., move the fluid from the inflatable members to the reservoir). For example, the user may repeatedly depress or squeeze the pump 306 until the deflation is completed. For example, squeezing the pump 306 may force fluid through valve 332. The pump 306 may then return to its original form, which provides a suction force causing fluid to be drawn into the pump 306 from the inflation member via valve 334. The fluid from the inflation member fills the pump 306 (or at least partially fills the pump 306). This pump cycle is repeated until the inflatable member is deflated.

Figure 25:
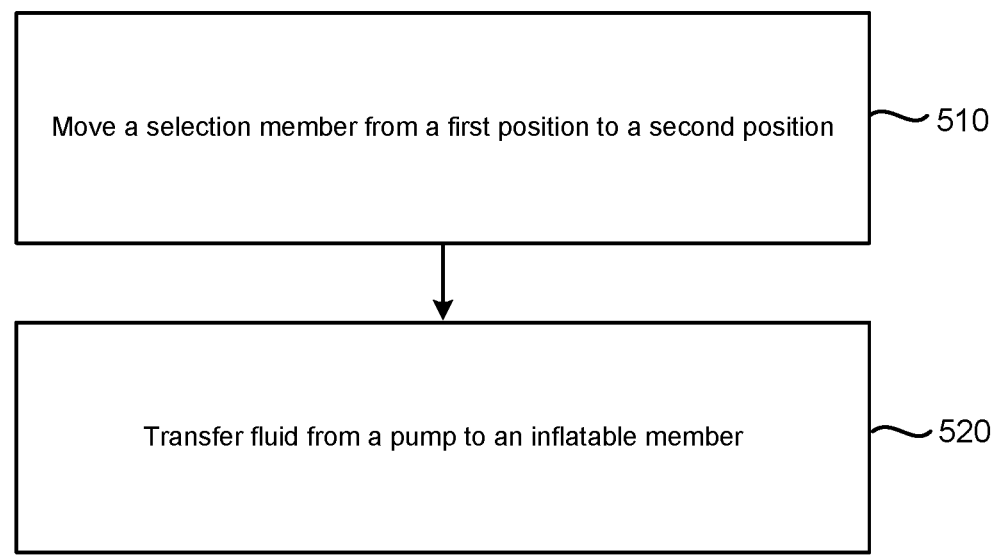
FIG. 25 is a flow chart of a method according to an embodiment.

FIG. 25 is a flow chart for a method 500 according to an embodiment. The method may be used to operate a penile implant. At 510, a user moves the selection member from a first position to a second position. In some embodiments, this places the implant in an inflation mode. At 520, the user can then transfer fluid from the pump of the device to the inflatable member. In some embodiments, this may be done by squeezing or otherwise actuating the pump. The user can then move the selection member from the second position to the first position to place the device in a deflate mode. The user can then move the fluid back to the reservoir by pumping the pump.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An inflatable penile prosthesis, comprising:
an inflatable member;
a reservoir configured to hold fluid; and
a pump assembly configured to facilitate a transfer of the fluid from the reservoir to the inflatable member when the prosthesis is in an inflation mode, and facilitate a transfer of the fluid from the inflatable member to the reservoir when the prosthesis is in a deflation mode, the pump assembly including:
a pump;
a valve body having a first valve, a second valve, a third valve, and a fourth valve; and
a selection member defining a lumen, the selection member being movable from a first position to place the prosthesis in the inflation mode by aligning the lumen of the selection member with at least two of the first, second, third and fourth valves, and a second position to place the prosthesis in the deflation mode by aligning the lumen of the selection member with at least two of the first, second, third and fourth valves.

2. The inflatable penile prosthesis of claim 1, wherein the lumen of the selection member is configured to be aligned with the first valve when the selection member is in the first position and is configured to be aligned with the second valve when the selection member is in the second position.

3. The inflatable penile prosthesis of claim 1, wherein the selection member is movably coupled to the valve body.

4. The inflatable penile prosthesis of claim 1, wherein the selection member is slidably coupled to the valve body.

5. The inflatable penile prosthesis of claim 1, wherein the first valve is a one-way valve.

6. The inflatable penile prosthesis of claim 1, wherein the first valve is a one-way duckbill valve.

7. The inflatable penile prosthesis of claim 1, wherein the lumen of the selection member is configured to be aligned with the first valve and the third valve when the selection member is in the first position and is configured to be aligned with the second valve and the fourth valve when the selection member is in the second position.

8. The inflatable penile prosthesis of claim 1, wherein the valve body includes a fifth valve and a sixth valve, the lumen of the selection member is configured to be aligned with the first valve, the third valve, and the fifth valve when the selection member is in the first position and is configured to be aligned with the second valve, the fourth valve, and the sixth valve when the selection member is in the second position.

9. The inflatable penile prosthesis of claim 1, wherein the valve body defines a first channel that fluidically couples the inflatable member and the pump, the valve body defines a second channel that fluidically couples the inflatable member and the pump, the first valve being disposed within the first channel, the second valve being disposed within the second channel.

10. The inflatable penile prosthesis of claim 1, wherein the valve body defines a first channel that fluidically couples the reservoir and the pump, the valve body defines a second channel that fluidically couples the reservoir and the pump, the first valve being disposed within the first channel, the second valve being disposed within the second channel.

11. The inflatable penile prosthesis of claim 1, wherein the inflatable member is a first inflatable member, further comprising a second inflatable member.

* * * * *